United States Patent [19]

Lippmann

[11] 4,118,495

[45] Oct. 3, 1978

[54] METHOD OF TREATING HYPERGLUCAGONEMIA WITH 1,3-DIOXO-1H-BENZ[DE]-ISOQUINOLINE-2(3H)-ACETIC ACID

[75] Inventor: Wilbur Lippmann, Montreal, Canada

[73] Assignee: Ayerst, McKenna & Harrison Limited, Montreal, Canada

[21] Appl. No.: 818,379

[22] Filed: Jul. 25, 1977

[51] Int. Cl.$^2$ .............................................. A61K 31/47
[52] U.S. Cl. ................................................... 424/258
[58] Field of Search ........................................ 424/258

[56] References Cited

U.S. PATENT DOCUMENTS

3,821,383  6/1974  Sestanj et al. ..................... 424/258

OTHER PUBLICATIONS

*Hackh's Chemical Dictionary* Fourth Edition, (1969), p. 30.

*Primary Examiner*—Frederick E. Waddell
*Attorney, Agent, or Firm*—Adley F. Mandel

[57] ABSTRACT

A method is disclosed for preventing or decreasing the secretion or availability of excessive amounts of glucagon in a human having abnormally increased levels of glucagon by administering an effective amount of 1,3-dioxo-1H-benz[de]isoquinoline-2(3H)-acetic acid.

4 Claims, No Drawings

METHOD OF TREATING HYPERGLUCAGONEMIA WITH 1,3-DIOXO-1H-BENZ[DE]-ISOQUINOLINE-2(3H)-ACETIC ACID

BACKGROUND OF THE INVENTION (a) Field of Invention

This invention relates to a method for preventing the secretion of excessive, i.e., absolute or relative, amounts of glucagon in humans suffering from hyperglucagonemia. Accordingly, the method of the invention is useful for relieving a complication arising from abnormally increased physiological availability of glucagon.

(b) Prior Art

Due to better diagnostic techniques, the state of abnormally increased levels or glucagon, i.e. hyperglucagonemia, in humans is being observed more often and its implications being better understood. For instance, hyperglucagonemia occurs in patients suffering from starvation, diabetes, severe infection or severe trauma, D. W. Wilmore et al., Lancet, 1, 73 (1974). In addition, hyperglucagonemia occurs in the surgical patients, severely burnt patients, elderly people and patients with alpha-cell carcinoma of the pancreatic islets, R. C. G. Russell et al., Br. Med. J., 1, 10 (1975); C. I. Orton, et al., Br. Med. J., 2, 170 (1975); J. Marco et al., paper no. 115 at the 37th Annual Meeting of the American Diabetic Association & Endocrine Meeting, Chicago, Illinois, June 5-7, 1977; and M. H. McGavran et al., N. Engl. J. Med., 274, 1408 (1966). Concerning the state of hyperglucagonemia, it is to be understood that this term not only refers to abnormally increased levels of glucagon as compared to normal levels, i.e. 100 pg or less per milliliter of serum (e.g. see Willmore et al., and Russell et al, cited above), but also includes the condition characterized by the presence of a physiologically inappropriate high level of glucagon.

It is now realized that hyperglucagonemia causes such undersirable effects as abnormalities in carbohydrate metabolism and excessive increases in protein catabolism and urinary urea excretion, see Russell et al., cited above. Therefore, a well tolerated agent capable of blocking glucagon release or availability in man would have clinical value in limiting the metabolic derangements of hypercatabolic states induced by hyperglucagonemia.

The active agent of this invention, 1,3-dioxo-1H-benz[de]isoquinoline-2(3H)-acetic acid, or a therapeutically acceptable salt thereof, is disclosed in U.S. Pat. No. 3,821,383, issued June 28, 1974. This active agent, hereinafter sometimes designated as "alrestatin", previously has been reported to be useful in preventing or relieving diabetic complications such as cataracts, neuropathy, nephropathy and retinopathy (see U.S. Pat. No. 3,821,383). I have now found unexpectedly that alrestatin, either in its free acid form or in its therapeutically acceptable salt form, is an inhibitor of glucagon release.

This finding, coupled with the fact that alrestatin is a relatively safe drug, renders the method of this invention particularly useful and advantageous.

SUMMARY OF THE INVENTION

According to this invention a method is provided for preventing or decreasing the secretion or availability of excessive amounts of glucagon in humans, which comprises administering to a human suffering from hyperglucagonemia an effective amount of 1,3-dioxo-1H-benz[de]isoquinoline-2(3H)-acetic acid, or a therapeutically acceptable salt thereof.

DETAILS OF THE INVENTION

According to the present method, alrestatin, either in its free acid form or in the therapeutically acceptable salt form, is employed as the active agent. Examples of suitable salt forms are described in U.S. Pat. No. 3,821,383 and include the sodium, potassium, magnesium, triethylamine and benzylamine salt forms. A preferred salt form is the sodium salt, i.e. alrestatin sodium.

Alrestatin, or a therapeutically acceptable addition salt thereof, is administered either orally or parenterally to humans suffering from hyperglucagonemia for the purpose of preventing the secretion of excessive amounts of glucagon. For many reasons oral administration is preferred.

While alrestatin or a therapeutically acceptable salt thereof can be administered along, e.g. as a sole component of a filled capsule, it is preferred to formulate the compound in various dosage forms for oral or parenteral administration, e.g. tablets, or sterile solutions. Such formulations are described in U.S. Pat. No. 3,821,383, herein incorporated by reference.

When utilizing alrestatin or one of its above-noted salt as agents for combatting or preventing hyperglucagonemia, the total dose of active agent can range from 1.0 to 1000 mg per kilogram of body weight per day with a preferred dosage range of from 50 to 500 mg per kilogram of body weight per day. Generally, a parenteral dose or an oral dose is administered in two to four application per day. Such doses are considered to be effective amounts when, following their administration, either the levels of glucagon are significantly reduced, or when the subjective symptons complained of by said human beings are reported as having disappeared, or being ameliorated or reduced in severity following such treatment.

The effectiveness of alrestatin or its therapeutically acceptable salts as agents for preventing hyperglucagonemia and inhibiting glucagon secretion or availability is demonstrated by the following experiment:

Male Sprague-Dawley rats (225-275 g; Canadian Breeding Laboratories, St. Constant, Quebec) were allowed access to food (Purina Lab Chow) and water ad lib for a minimum of 5 days before experiments were conducted. After light diethyl ether anaesthetization, the animals were injected with a bolus of saline or alrestatin (sodium salt form in 0.3 ml saline/100 g of body weight) in the external jugular vein followed immediately with a bolus of arginine-HCl (British Drug House) at a dose of 100 mg/100 g of body weight, cf. M. Brown et al., Endocrinology, 98, 336 (1976). Vehicle control animals received a second injection of saline. Five minutes later trunk blood was collected by decapitation into chilled tubes containing sodium heparin (Upjohn) and aprotinin (Trasylol, *Boehringer-Ingelheim) (20 U and 1000 KIU per ml whole blood, respectively). Plasma was collected after centrifugation, stored at −20° C. and assayed for immunoreactive glucagon and insulin glacagon within 2 weeks.

*Trademark

Plasma insulin was assayed with antiserum to rat insulin[125]. I-Insulin tracer was purchased from New England Nuclear, Lachine, Quebec, and purified before use on a DEAE-cellulose column (J. D. Curtis, M.SC. Thesis, McGill University, Montreal, Quebec, Canada, 1968). Rat insulin purchased from Novo A/S, Copenhagen, Denmark, was used as unlabelled standard. Plasma glucagon was assayed by the method of G. R. Faloona and R. H. Unger in "Methods of Hormone Radioimmunoassay", J. Behmann, Ed., Academic Press, New York, N.Y., 1974, with two modifications, i.e., the tubes were not precoated with gelatin, and normal lamb serum was omitted from the glycine buffer; these modifications did not alter the binding of glucagon or the non-specific binding. Glucagon antiserum (Antiserum 30K, purchased from Dr. R. H. Unger, Houston, Texas) was employed in the assay. $I^{125}$-Glucagon purchased from Nuclear Medical Laboratories, Dallas, Texas, was purified according to the method of K. H. Jorgensen and O. D. Larsen, Horm. Metab. Res., 4, 223 (1972). Procine glucagon, which has been demonstrated to be identical to rat glucagon, F. Sundby and J. Markussen, Horm. Metab. Res., 3, 184 (1971), was purchased from Novo A/S and was used as the standard. Antibody bound hormone was separated from free hormone by conventional charcoal-dextran methods.

Regarding glucagon response, arginine (100 mg/100 g of body weight) stimulated glucagon release to a mean of about 100 pg/ml above the plasma hormone concentration in the vehicle-treated animals (arginine: 284.8 ± 13.7 vs vehicle: 180.6 ± 5.8 pg/ml. Alrestatin sodium administered immediately before arginine decreased the glucagon concentrations in a range examined, i.e., 35–200 mg/Kg; alrestatin sodium at 200 mg/Kg completely prevented the increase caused by arginine.

Regarding insulin response, arginine administration increased the plasma insulin concentration by about 100 μU/ml. Alrestatin sodium increased the insulin release observed with arginine in the range examined, i.e., 35–200 mg/Kg; the insulin release was increased by about 2.5 fold by alrestatin sodium at 200 mg/Kg.

It is noteworthy that in catabolic states from starvation, diabetes, severe infection and severe trauma, plasma glucagon is high in relation to insulin (see Wilmore, cited above). Such states tend to increase the use of aminoacids for gluconeogenesis and ureagenesis at the expense of protein biosynthesis, R. H. Unger, Diabetes, 20, 834 (1972). Consequently, as shown by the above experiment, the method of this invention benefits the hyperglucagonemia patient by tending to normalize the relation of glucagon and insulin.

Finally, the $LD_{50}$ of alrestatin in rats according to the route of administration is greater than 2,500 mg/kg (perorally); 1220 ± 45 mg/kg (intravenously); and 1380 ± 80 mg/kg (intraperitoneally). Therefore, a good therapeutic index of safety is present.

I claim:

1. A method for preventing or decreasing the secretion or availability of excessive amounts of glucagon in humans, which comprises: administering to a human suffering from hyperglucagonemia an effective amount of 1,3-dioxo-1H-benz[de]isoquinoline-2(3H)-acetic acid, or a therapeutically acceptable salt thereof.

2. The method of claim 1 in which the effective amount of 1,3-dioxo-1H-benz[de]isoquinoline-2(3H)-acetic acid in within the range of from 1.0 to 1000 mg per kilogram of body weight.

3. The method of claim 1 in which the effective amount of 1,3-dioxo-1H-benz[de]isoquinoline-2(3H)-acetic acid is within the range of 50 to 500 mg per kilogram of body weight.

4. The method of claim 1 in which the therapeutically acceptable salt is the sodium salt.